United States Patent [19]

Paes

[11] Patent Number: 5,660,200
[45] Date of Patent: Aug. 26, 1997

[54] DOUBLE-VALVED VARIABLE PRESSURE DEVICE FOR HYDROCEPHALY

[75] Inventor: Newton Paes, Sao Paulo, Brazil

[73] Assignee: Phoenix Biomedical Corporation, Norristown, Pa.

[21] Appl. No.: 347,304

[22] PCT Filed: May 3, 1994

[86] PCT No.: PCT/BR94/00017

§ 371 Date: Apr. 26, 1995

§ 102(e) Date: Apr. 26, 1995

[87] PCT Pub. No.: WO95/29715

PCT Pub. Date: Nov. 9, 1995

[51] Int. Cl.$^6$ ............ F16K 31/36; A61M 27/00
[52] U.S. Cl. ............ 137/110; 137/505.13; 137/512.1; 137/844; 137/845; 604/9; 604/247
[58] Field of Search ............ 137/110, 505.13, 137/512.1, 845, 849, 844; 604/9, 247

[56] References Cited

U.S. PATENT DOCUMENTS

| | | | |
|---|---|---|---|
| 3,385,637 | 5/1968 | Kersting | 137/110 |
| 3,547,498 | 12/1970 | Bueler | 137/110 X |
| 3,782,405 | 1/1974 | Potts | 137/110 |
| 4,068,680 | 1/1978 | Sliger | 137/512.1 |
| 4,621,654 | 11/1986 | Holter | 132/38 |
| 4,675,003 | 6/1987 | Hooven | 604/9 |
| 4,681,559 | 7/1987 | Hooven | 137/512.1 X |
| 4,776,838 | 10/1988 | Saint-Rose et al. | 604/9 |
| 4,787,887 | 11/1988 | Saenz Arroyo | 604/9 |

Primary Examiner—John Rivell
Attorney, Agent, or Firm—Brinks Hofer Gilson & Lione

[57] ABSTRACT

The present invention relates to a double-valved variable pressure device for hydrocephaly having a vertical capsule with sloped ends ending in upper and lower coupling sectors appropriate for connection to a proximal catheter and a distal catheter that constitute the input and output for a cephalo-rachidian liquid through the body. The liquid or volume has its pressure controlled by means of two valves which maintain a constant drained volume along a wide range of pressures the device is submitted to.

1 Claim, 1 Drawing Sheet

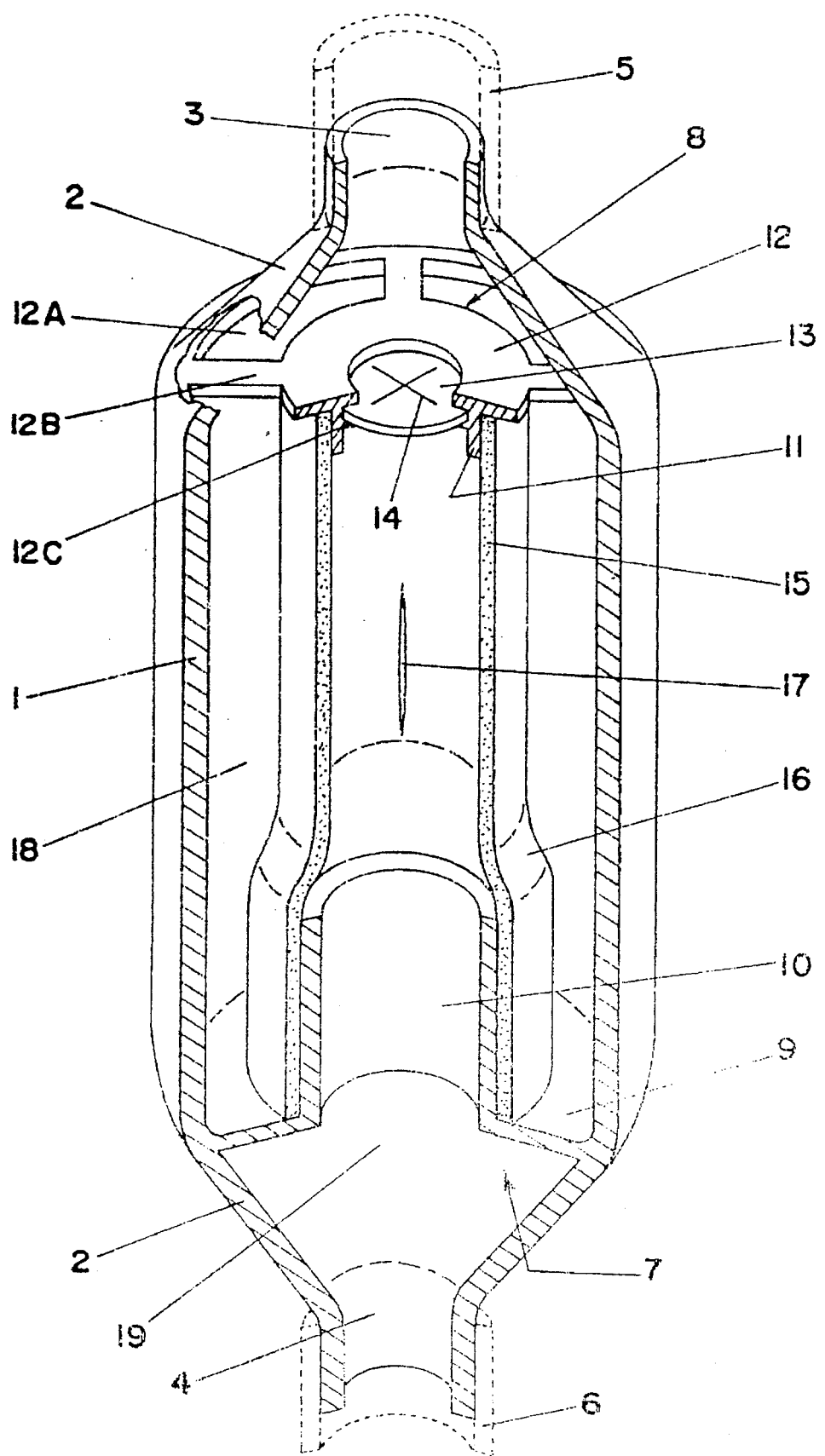

DOUBLE-VALVED VARIABLE PRESSURE DEVICE FOR HYDROCEPHALY

BACKGROUND OF THE INVENTION

This invention relates to a double-valved variable pressure device for hydrocephaly. More particularly, the present invention relates to technical and functional improvements to the operation of a valve for hydrocephaly used under medical conditions demanding the removal of cephalo-rachidian liquid out of the central nervous system in an attempt to maintain a stable and proper intracranial pressure.

As is already known by specialists in this area, there are currently numerous types of apparatus for the above-referenced purpose. In most cases, these devices have only one valved element and, accordingly, the control of outflow and cephalo-rachidian liquid pressure are solely and exclusively dependent on the perfect operation of only one valve. This type of apparatus has several disadvantages such as: a) the proper relationship between the volume of drained liquid and the intracranial pressure is not managed; and b) these devices produce the phenomenon of hyperdrainage (the siphon effect), with important medical complications that are described in the literature.

SUMMARY OF THE INVENTION

The present invention provides for a double-valved variable pressure device for overcoming the aforementioned disadvantages. The present invention achieves the cephalo-rachidian pressure and the outflow control by two valves implementing a new operational concept. The first valvular element determines the system's outflow until a given "minor" pressure (i.e., the intracranial pressure) propagated by means of the liquid means into the device, exerting a closing force on the first valve. Accordingly, the higher the pressure at this part of the device, the more the valve will be closed, until it is fully closed. At this time the intracranial pressure is released through a second valve that, similar to the first valve, permits the liquid to be properly drained and, this "higher" pressure being stopped, the second valve will automatically close while the first valve returns to its former "open" state and the cycle is once again repeated. This double-valved operation lends itself to a number of technical and practical advantages, among which are: a) no hyperdrainage phenomenon is allowed; b) the outflow permitted by the system is directly related to the intracranial pressure the patient is submitted to; c) the system is continuously self-adjustable by means of two valves; and d) the cephalo-rachidian liquid pressure and outflow do not depend on just one valve system, but rather on two balanced systems, which make possible a more precise and proper control for each patient.

The present invention will be best understood by reference to the detailed description made below in conjunction with the attached drawing.

BRIEF DESCRIPTION OF THE DRAWING

The attached drawing illustrates a perspective cutaway view showing the internal and external details of the present invention.

DETAILED DESCRIPTION OF A PREFERRED EMBODIMENT

As shown in the figure and its details, this double-valved variable pressure device for hydrocephaly consists of a frame in the shape of a capsule 1 constructed of a non-deformable material, substantially in vertical cylindrical shape, with sloped ends ending in upper coupling sectors and lower sectors 4 appropriate for the connection of a proximal 5 and distal 4 catheter. The proximal and distal catheters constitute the input and output for the cephalo-rachidian liquid through the body or capsule 1. The body or capsule 1 is internally provided with two annular sectors, a lower 7 one and upper 8 one. Both of the annular sectors 7, 8 are made of a rigid and undeformable material. The lower sector 7 forms a waterproof closing through a flange 9 and has its outer diameter integrated into the capsule wall 1. The inner diameter of the lower sector 7 is integrated with an upward vertical tubular short sector 10 that, in turn, is coaxially aligned with another similar sector with a smaller diameter 11. The other similar sector with a smaller diameter 11 is also integrated to a flange 12, although in this case the flange presents several openings 12A such that it is connected to the capsule wall 1 through a number of radial extensions 12B. Additionally, its inner diameter presents a double-wall configuration 12C enclosing a second valve in the form of a complacent disc 13 with a cross-centered view 14. The first valve is defined by a tubular element made of a resilient material 15 having an inner diameter relatively equal to the external diameter of the upper coupling sector 11. Because the lower coupling sector 10 presents a diameter substantially larger than the inner diameter of the tube 15, the tube 15 is provided with an elastic deformation 16. The complacent tube 15 presents a lengthwise slot 17 positioned in the tube 15 that is maintained in an open position by the deformation 16. The tension forces appearing in the complacent portion of the tube wall 15 due to the deformation result in the opening of the slot 17. The first and second valves define two chambers for the cephalo-rachidian liquid. The first chamber is defined as a retention and control chamber 18 and the second chamber is an outflow chamber 19.

The operation of the present invention is extremely simple. The intraventricular liquid reaches the inner section of the capsule through the proximal catheter 5 and floods the first chamber 18. Under these conditions, the first outflow via for the cephalo-rachidian liquid is defined through the lengthwise slot 17, held open by the above-mentioned tension forces, such that the cephalo-rachidian liquid controllably flows out into the chamber 19. Thus the slot 17, in accordance with its area, determines the effect of the system's outflow adjusting valve because the intracranial pressure propagated through the liquid means into the chamber 18 exerts a closing force on the tube wall 15 with resulting variation in the slot area. This variation of area is inversely proportional to the loss of the system's load, the flow being kept constant under the several pressures the system might be subject to. However, if the pressure reaches a maximum level, the slot 17 is completely closed at which time the second valve 13 starts operating. In this manner, the cephalo-rachidian liquid also flows out to the chamber 19 until the pressure falls again to such an extent to open the slot 17 and close the second valve again. At this time the operational cycle is started once again with no risk of the hyperdrainage phenomenon occurring.

Finally, the cephalo-rachidian liquid resulting from the valvular system is drained by the distal catheter 6. The distal catheter 6 is applied into a biological cavity or an external area according to the preference and professional experience of the physician using this prosthesis.

I claim:

1. A double-valved variable pressure device for hydrocephaly comprising:

a frame in the form of a capsule constructed of a non-deformable material, the capsule having a substantially vertically oriented cylindrical shape;

the capsule having first and second ends wherein the first end defines an upper coupling sector and the second end defines a lower coupling sector, each of the coupling sectors designed for connection to a proximal and a distal catheter, whereby the proximal and distal catheters comprise an input and an output for a cephalo-rachidian liquid; a lower and an upper annular sector positioned inside the capsule, each of the annular sectors constructed of a rigid and non-deformable material, the lower annular sector forming a waterproof closing through a flange wherein the external diameter of the lower annular sector is integral with the capsule wall and the inner diameter of the lower annular sector is integral with an upward vertical tubular short sector;

the upward vertical tubular short sector coaxially aligned with a second sector having a smaller diameter than the upward vertical tubular short sector, the second sector connected to a second flange and linked to the capsule wall by a plurality of extensions defining a plurality of openings between the second flange and the capsule wall;

the second sector having an inner diameter defining a double-wall configuration enclosing a second valve;

a tubular element constructed of a resilient material and having a longitudinal slot defining a first valve, the tubular element connecting the upward vertical short sector to the second sector, the tubular element having an inner diameter that is substantially equal to the external diameter of the second sector and less than the external diameter of the upward vertical tubular short sector, wherein an elastic deformation of the resilient tube opens the longitudinal slot, whereby the elastic deformation initially maintains the first valve in an open position; and wherein the first and second valves define a retaining and control chamber and an outflow chamber inside the capsule.

* * * * *